United States Patent
Crosby et al.

(10) Patent No.: US 10,012,604 B2
(45) Date of Patent: Jul. 3, 2018

(54) XRF DETECTOR AND SOURCE CALIBRATION APPARATUS

(71) Applicant: THERMO GAMMA-METRICS PTY LTD, Adelaide Airport (AU)

(72) Inventors: Bryan John Crosby, Adelaide (AU); Simon Liemar, Adelaide (AU); Peter William Hayles, Adelaide (AU); Charlie Minghua Mao, Adelaide (AU); Tejas Indravadanbhai Shah, Adelaide (AU); Hao Zeng, Adelaide (AU)

(73) Assignee: THERMO GAMMA-METRICS PTY LTD, Adelaide Airport (AU)

( * ) Notice: Subject to any disclaimer, the term of this patent is extended or adjusted under 35 U.S.C. 154(b) by 179 days.

(21) Appl. No.: 14/969,811

(22) Filed: Dec. 15, 2015

(65) Prior Publication Data
US 2017/0167990 A1  Jun. 15, 2017

(51) Int. Cl.
*G01N 23/223*  (2006.01)

(52) U.S. Cl.
CPC .................................. *G01N 23/223* (2013.01)

(58) Field of Classification Search
CPC ........... G01N 23/223; G01N 2223/076; G01N 2223/01; G01N 23/22; G01N 2223/1016; G01N 23/2076; G01N 23/2252; G01N 2021/646; G01N 21/64; G01N 23/20025; A61B 6/4464; A61B 6/4845; A61B 6/485
USPC .................... 378/44, 45, 48, 6, 197
See application file for complete search history.

(56) References Cited

U.S. PATENT DOCUMENTS

| | | | |
|---|---|---|---|
| 3,433,954 A | 3/1969 | Bowman | |
| 6,522,718 B2 | 2/2003 | Sato | |
| 2008/0156996 A1 | 7/2008 | Nicolosi et al. | |
| 2015/0234060 A1* | 8/2015 | Rinsema | G01T 7/08 |
| | | | 378/44 |

FOREIGN PATENT DOCUMENTS

| | | |
|---|---|---|
| CN | 103808746 A | 5/2014 |
| DE | 10133676 A1 | 6/2002 |
| DE | 10200237 A1 | 7/2003 |
| DE | 112009000004 | 7/2010 |

OTHER PUBLICATIONS

Fernandes et al., "X-ray spectrometry with Peltier-cooled large area avalanche photodiodes", Nuclear Instruments and Methods in Physics Research B 213 (2004) 267-271.

* cited by examiner

*Primary Examiner* — Don Wong
(74) *Attorney, Agent, or Firm* — William R. McCarthy, III

(57) ABSTRACT

An apparatus includes at least one X-ray source that emits X-rays toward a sample, an X-ray fluorescence (XRF) detector that detects X-ray radiation scattered from the sample, an internal standard that emits scattered X-ray radiation in response to X-rays emitted from the at least one X-ray source, and a carriage assembly that translates the at least one X-ray source and XRF detector between a sample measurement position and an internal standard measurement position.

23 Claims, 7 Drawing Sheets

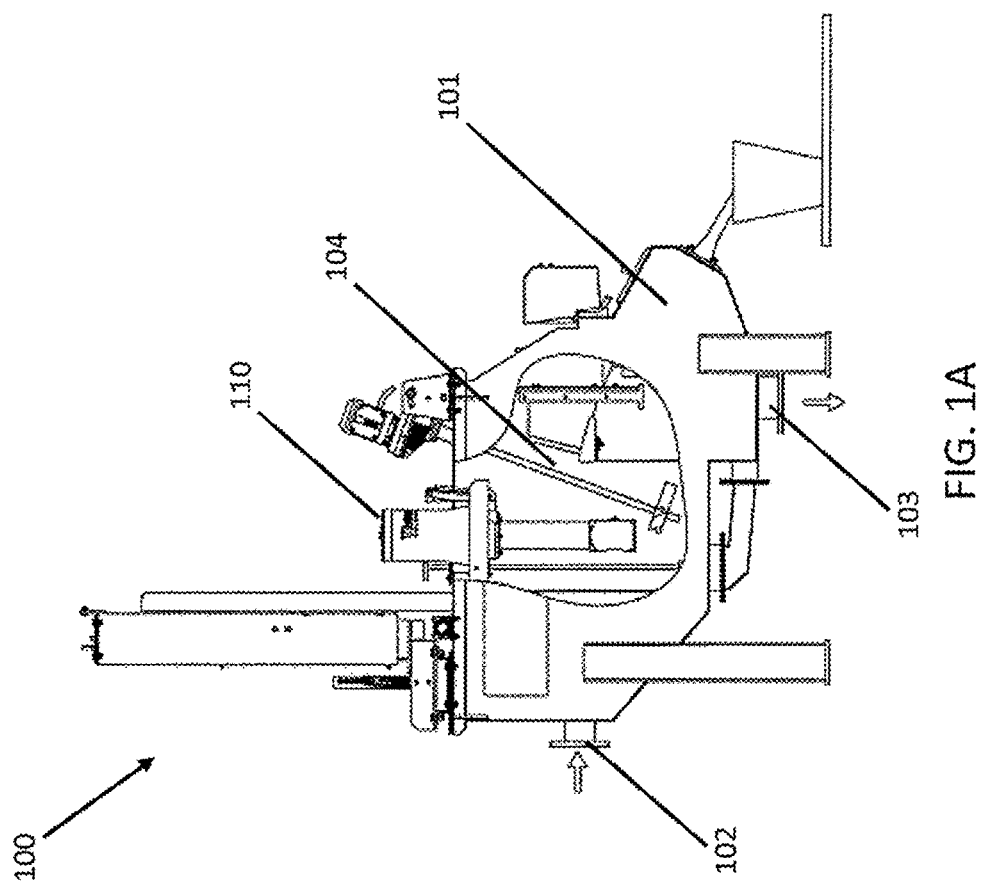

XRF DETECTOR AND SOURCE CALIBRATION APPARATUS

FIELD OF THE INVENTION

The invention is generally related to an X-ray fluorescence detector and source calibration apparatus and method.

BACKGROUND

In mineral ore processing plants associated with mining operations, online sampling and analysis stations typically provide continuous in-stream analysis of composite samples for metallurgical accounting, enabling plant operators to follow and respond to process trends in real time. Such sampling and analysis stations generally include an inlet, an outlet, a stirrer, and a dedicated immersion probe analyzer mounted into the final tank of a full-flow sampling station designed to present to the analyzer a representative sample of the main ore slurry stream. The integrated immersion probe analyzer provides simultaneous analysis of typically up to 20 elements and percent solids in the slurry. Elements from calcium (Ca) to uranium (U) in the periodic table are measured by the immersion probe analyzer that typically includes a multi-element probe (MEP) using X-ray fluorescence (XRF), a proven and robust technology for plant environments.

In an XRF measurement using the immersion probe analyzer, the MEP uses an X-ray source to excite fluorescent X-rays from elements in the mineral ore slurry. Each element in the ore slurry emits fluorescent X-rays of an energy and intensity that is characteristic of that element and its concentration. Fluorescent and scattered X-rays from the ore slurry impinge on the detector of the MEP to produce small electrical pulses that are shaped, amplified, and counted. The peak amplitude of the pulse is proportional to the energy of the incident X-ray. The scattered X-rays are used to provide measurements of the ore slurry density. The number of X-rays is proportional to the elemental concentration in the ore slurry.

The immersion probe analyzer is calibrated for the particular product stream using a suite of calibration samples, collected over a period of time and covering the range of plant operating variables and conditions likely to be encountered in the stream. These calibration samples are presented to the probe head as external standards, and are then chemically assayed in a laboratory either on-site or elsewhere for metal concentration and percent solids, and the assays are then correlated with the corresponding count-rates from the probe that were measured during the period that the sample was taken.

In online sampling and analysis providing continuous in-stream analysis of composite samples for metallurgical accounting, the count-rates from the probe need to be normalized to account for long term changes in the performance of the probe due to such factors as X-ray source decay and detector efficiency. This normalization can in theory be performed using an external standard, monitoring the count-rates of the probe to the same standard over time. However, measuring an external standard requires removing the probe from the ore slurry stream, cleaning the probe, and then attaching the external standard, which is time consuming and reduces the operating efficiency of the probe.

Therefore, there is a need for an XRF detector and source calibration apparatus that reduces or eliminates the problems described above.

SUMMARY

In one embodiment, an apparatus includes at least one X-ray source that emits X-rays toward a sample, an X-ray fluorescence (XRF) detector that detects X-ray radiation scattered from the sample, an internal standard that emits scattered X-ray radiation in response to X-rays emitted from the at least one X-ray source, and a carriage assembly that translates the at least one X-ray source and XRF detector between a sample measurement position and an internal standard measurement position. The at least one X-ray source can be one or more of a Curium-244 (Cm-244) source, a Plutonium-238 (Pu-238) source, an Americium-241 (Am-241) source, a Cadmium (Cd-109) source, an Iron-55 (Fe-55) source, or any combination thereof. In some embodiments, the internal standard measurement position can be a fail-safe position.

In certain embodiments, the internal standard can include a mineral sample powder, such as one of silica, haematite, chalcocite, or any combination thereof. The amount of scattered X-ray radiation emitted by the internal standard in response to X-rays emitted from the at least one X-ray source can be consistent to less than or equal to 3 parts in a thousand between measurements. In some embodiments, the XRF detector can be one of a silicon drift detector or a PIN diode detector.

In another embodiment, a method of monitoring an XRF detector response to an X-ray source in an immersion probe analyzer includes providing at least one X-ray source that emits X-rays toward a sample, detecting X-ray radiation scattered from the sample with an X-ray fluorescence (XRF) detector, providing an internal standard that emits scattered X-ray radiation in response to X-rays emitted from the at least one X-ray source, translating a carriage assembly including the at least one X-ray source and XRF detector into an internal standard measurement position, and determining whether the amount of X-ray radiation scattered in response to X-rays emitted from the at least one X-ray source is consistent between measurements. The method further includes translating the carriage assembly including the at least one X-ray source and XRF detector into a sample measurement position. The method can further include initiating diagnostic testing of the immersion probe analyzer if the amount of scattered X-ray radiation emitted by the internal standard in response to X-rays emitted from the at least one X-ray source is inconsistent between measurements. The at least one X-ray source, internal standard measurement position, internal standard, and XRF detector are as described above. The stability criteria for the internal standard are described below.

In yet another embodiment, an XRF immersion probe analyzer includes a probe head immersible into and resistant to an ore slurry, the probe head including an X-ray transparent window. The XRF immersion probe analyzer further includes a probe including at least one X-ray source that emits X-rays toward a sample through the window, an X-ray fluorescence (XRF) detector that detects X-ray radiation scattered from the sample through the window, an internal standard that emits scattered X-ray radiation in response to X-rays emitted from the at least one X-ray source, and a carriage assembly that translates the at least one X-ray source and XRF detector between a sample measurement position in the probe head and an internal standard measurement position.

The invention has many advantages, such as enabling the normalization of count-rates from the probe to account for long term changes in the performance of the probe due to such factors as X-ray source decay and detector efficiency without removing the probe from the ore slurry stream.

BRIEF DESCRIPTION OF THE DRAWINGS

FIG. 1A is a schematic illustration of an online sampling and analysis station including an exemplary embodiment of an XRF immersion probe analyzer according to the invention.

Like reference numerals refer to corresponding parts throughout the several views of the drawings.

DETAILED DESCRIPTION OF EMBODIMENTS

Figure 1C:
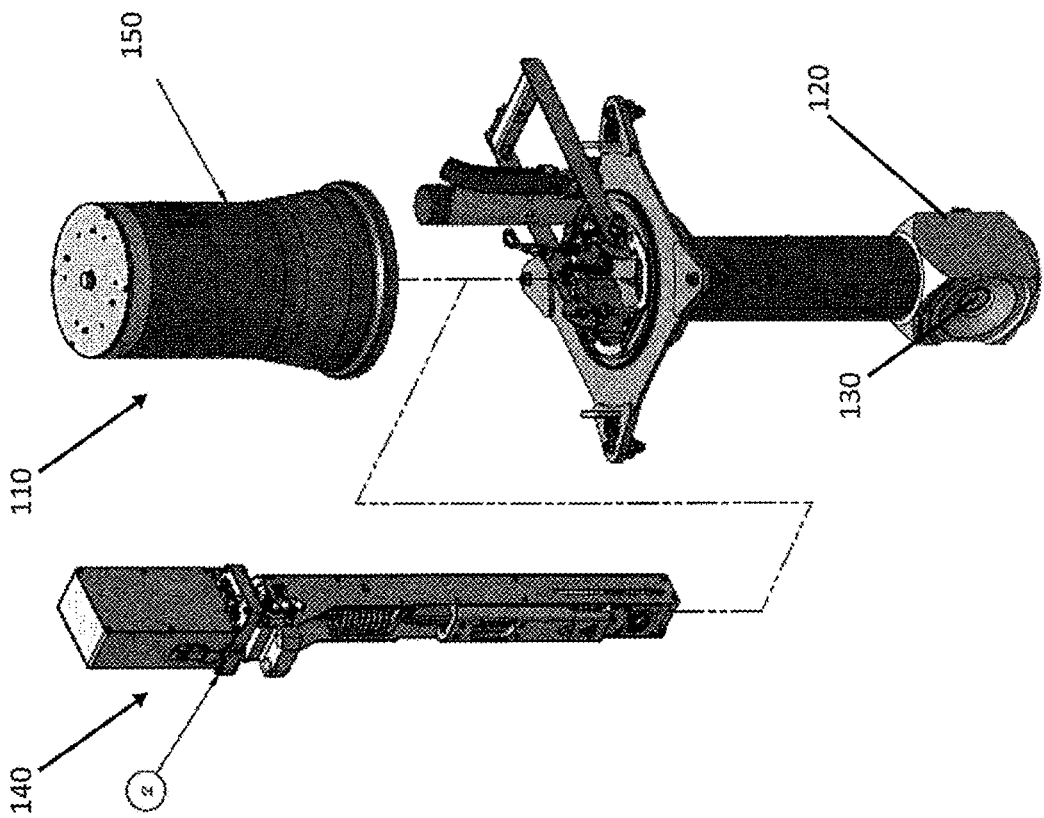
FIG. 1C is an exploded view of an exemplary embodiment of an XRF immersion probe analyzer including a probe according to the invention.

In the description of the invention herein, it is understood that a word appearing in the singular encompasses its plural counterpart, and a word appearing in the plural encompasses its singular counterpart, unless implicitly or explicitly understood or stated otherwise. Any references to one element are not limited to only one element, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. Additionally, it will be understood that any list of such candidates or alternatives is merely illustrative, not limiting, unless implicitly or explicitly understood or stated otherwise. In addition, unless otherwise indicated, numbers expressing quantities of ingredients, constituents, reaction conditions and so forth used in the specification and claims are to be understood as being modified by the term "about."

Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

In one embodiment shown in FIG. 1A, an online sampling and analysis station 100 includes a housing 101 having a slurry inlet flange 102 and a slurry outlet flange 103, and a stirrer 104 that stirs the slurry within the housing 101 to present a homogeneous mixture to an XRF immersion probe analyzer 110. As shown in FIG. 1B, the XRF immersion probe analyzer 110 includes a probe head 120 immersible into and resistant to an ore slurry. The probe head 120 includes an X-ray transparent window 130, that is typically made of 50 μm thick Mylar.

Figure 1B:
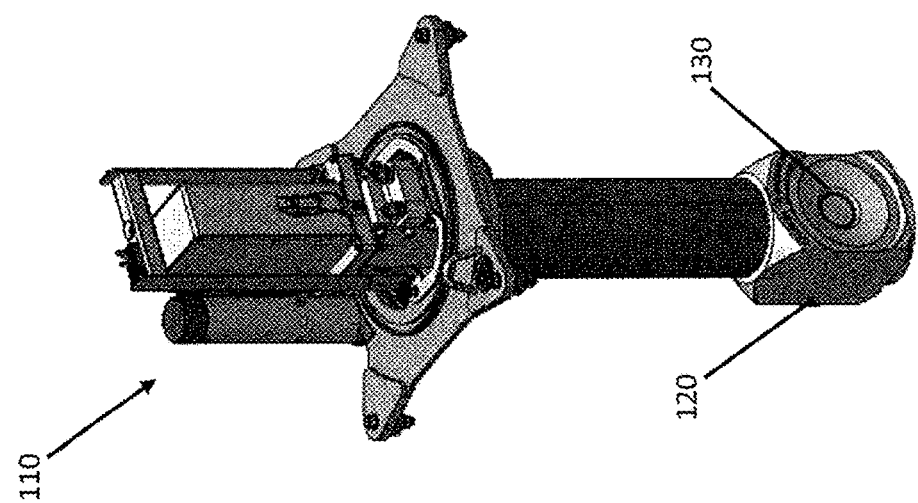
FIG. 1B is an illustration of an exemplary embodiment of an XRF immersion probe analyzer according to the invention.
Figure 1D:
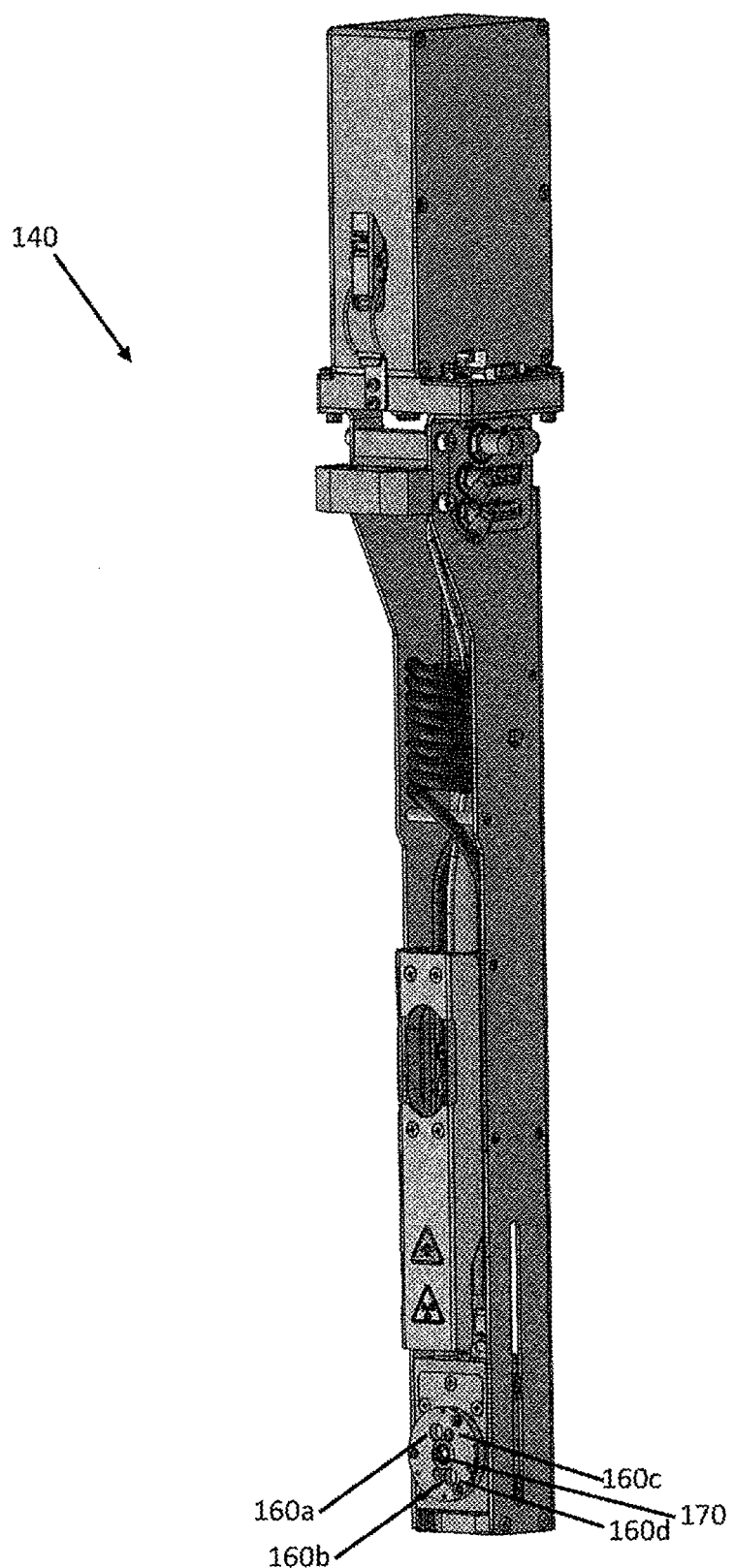
FIG. 1D is an illustration of an exemplary embodiment of a probe according to the invention.

As shown in FIG. 1C, the XRF immersion probe analyzer 110 further includes a probe 140, and a cap 150 that seals the probe 140 inside the probe head 120. As shown in FIG. 1D, the probe 140 includes at least one X-ray source 160, four examples (160a, 160b, 160c, and 160d) of which are shown in FIG. 1D. The X-ray sources 160a-d emit X-rays toward a sample through the window 130 shown in FIGS. 1B and 1C. A variety of X-ray sources are suitable, such as Curium-244 (Cm-244) source, a Plutonium-238 (Pu-238) source, an Americium-241 (Am-241) source, a Cadmium (Cd-109) source, an Iron-55 (Fe-55) source, or any combination thereof.

Figure 2B:
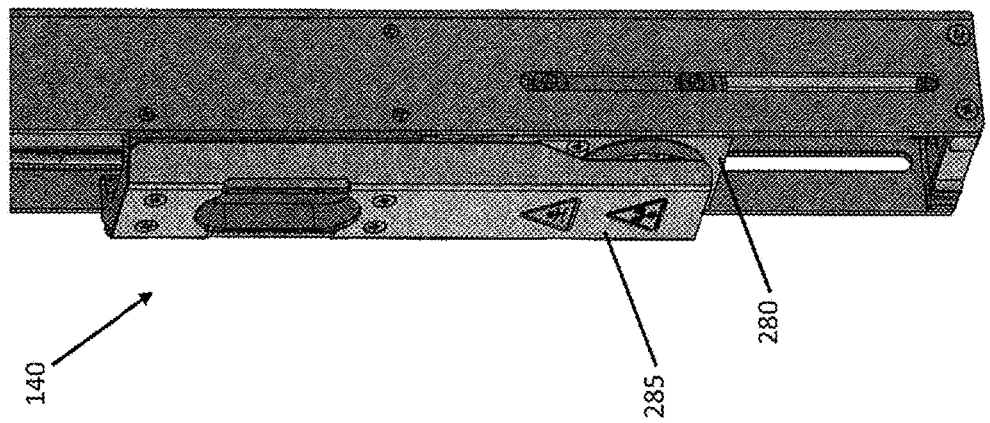
FIG. 2B is an illustration of an exemplary embodiment of a probe according to the invention in the internal standard measurement position.
Figure 2A:
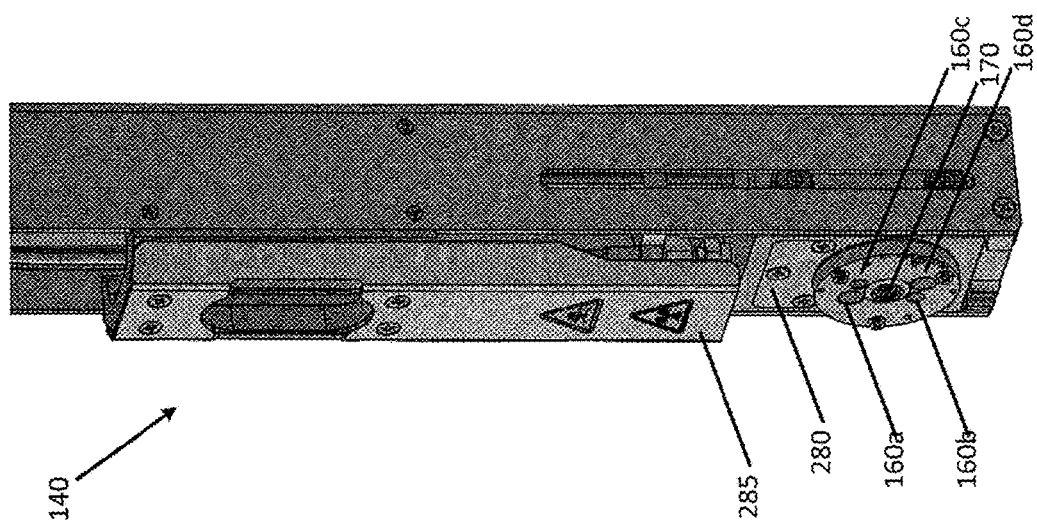
FIG. 2A is an illustration of an exemplary embodiment of a probe according to the invention in the sample measurement position.

Turning back to FIG. 1D, the probe 140 also includes an X-ray fluorescence (XRF) detector 170 that detects X-ray radiation scattered from the sample through the window 130 shown in FIGS. 1B and 1C. Suitable XRF detectors include silicon drift detectors or PIN diode detectors. As shown in FIGS. 2A and 2B, X-ray sources 160a-160d and XRF detector 170 are mounted on a carriage assembly 280 that translates the X-ray sources and XRF detector between a sample measurement position shown in FIG. 2A, and an internal standard measurement position shown in FIG. 2B and described further below, in which the X-ray sources and XRF detector are covered by a shield 285.

Figure 2C:
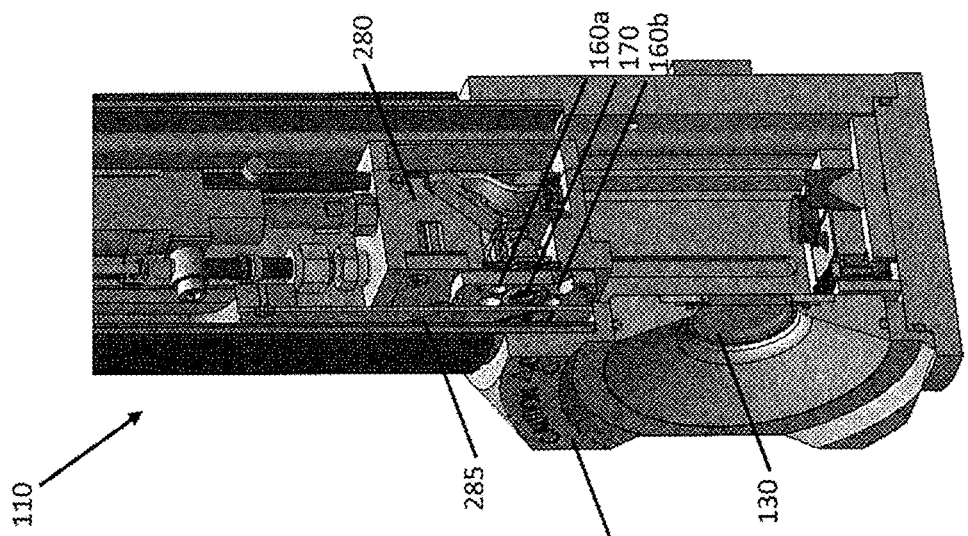
FIG. 2C is a cross section of an exemplary embodiment of a probe according to the invention in the sample measurement position in an XRF immersion probe analyzer.
Figure 2D:
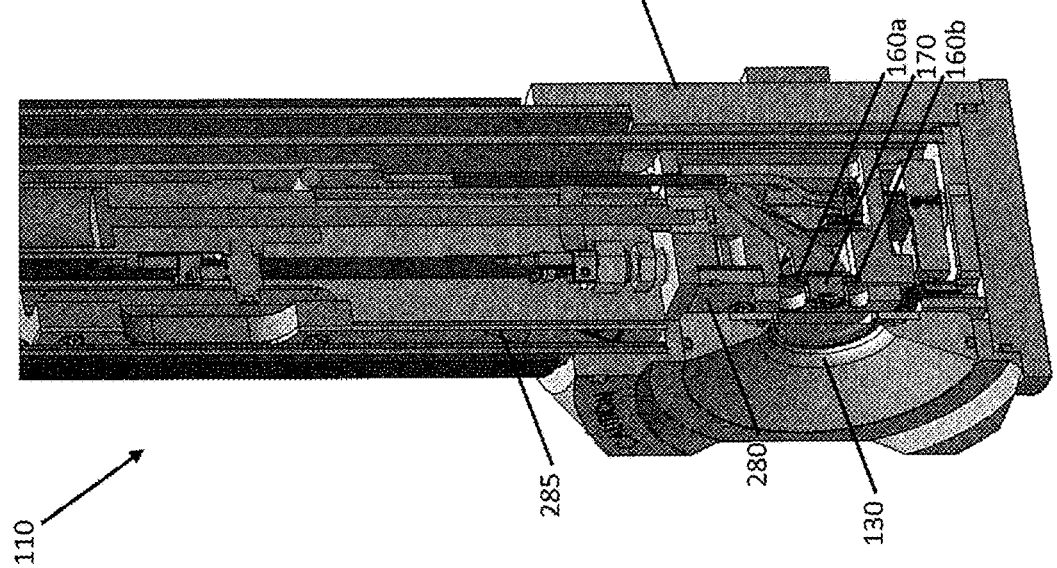
FIG. 2D is a cross section of an exemplary embodiment of a probe according to the invention in the internal standard measurement position in an XRF immersion probe analyzer.

As shown in FIG. 2C, the carriage assembly 280 is located in the probe head 120 of the immersion probe analyzer 110 in the sample measurement position, so that X-ray sources 160 (two sources 160a and 160b shown in cross section in FIG. 2C) and detector 170 can measure X-ray radiation scattered from the sample through the window 130. As shown in FIG. 2D, the carriage assembly 280 is located inside the immersion probe analyzer 110 in the internal standard measurement position, with the X-ray sources 160a-160d and XRF detector 170 facing the shield 285.

Figure 3:
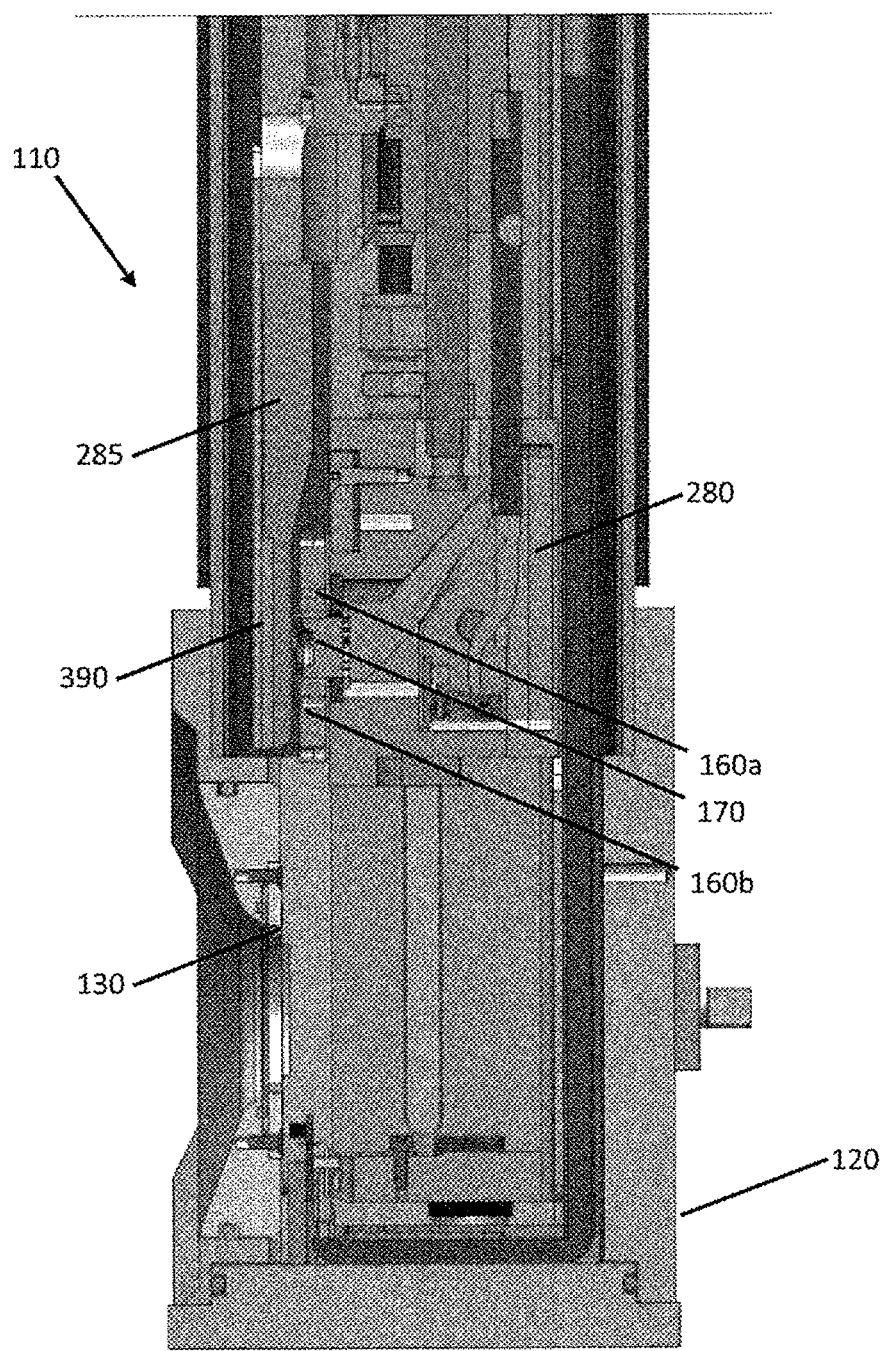
FIG. 3 is a cross section of an exemplary embodiment of a probe including an internal standard according to the invention in the internal standard measurement position in an XRF immersion probe analyzer.

Turning to FIG. 3, the shield 285 includes an internal standard 390 that emits scattered X-ray radiation in response to X-rays emitted from the X-ray sources 160 (two sources 160a and 160b shown in cross section in FIG. 2C). In one embodiment, the internal standard 390 is a composite material comprising mineral species, such as one of silica, haematite, chalcocite, or any combination thereof, and a thermoset polymer, such as a low viscosity epoxy resin and hardener, mixed according to the resin manufacturer's directions.

In one exemplary embodiment, the thermoset polymer is placed in a vacuum to remove excess moisture and air bubbles, and then mixed with crushed mineral powder, typically composed of particles with maximum diameters of 200 µm. Each grain of the crushed mineral powder is typically dominated by a single mineral species, although many mineral species can be present in the sample powder. In some embodiments, the concentration of copper oxide in a sample can vary from 0.01% to 50% by weight. The relative proportions of each mineral species are arranged to reflect the relative proportions present in the sample streams which will be analyzed by the immersion probe analyzer in actual use.

The total minerals content of the internal standard is balanced with the thermoset polymer content in order to make a smooth air-free internal standard having a substantial concentration of minerals to be detected by the XRF detector. In one exemplary embodiment, the concentration of minerals is 25 vol % and the remaining constituents are thermoset polymer constituents comprising hardener and resin. The ratio of hardener to resin is typically according to the polymer manufacturer's directions for maximum strength. For example, for Ciba Geigy low viscosity epoxy, the recommended ratio is one part Hy956 and 4 parts LC151. Once mixed, the mixture is poured into a mould of a suitable shape and thickness, such as, for example, a rectangle 3 mm thick, 70 mm long, and the width of the shield 285 (see FIG. 2B).

Turning back to FIG. 3, the amount of scattered X-ray radiation emitted by the internal standard 390 in response to X-rays emitted from the at least one X-ray source 160 (two sources 160a and 160b shown in cross section in FIG. 3) is measured by XRF detector 170, and should be consistent to within a set stability criterion, such as, in one exemplary embodiment, less than or equal to 3 parts in a thousand (0.3%) between measurements. For an internal standard measurement time of, for example, 300 seconds, the ratio between the measurement standard deviation and the average count rate for all measurements over a period of time in a range of between 8 hours and 48 hours, such as a 24 hour period, should be less than or equal to the set stability criterion, e.g., 3 parts in a thousand (0.3%). Additional or alternative uses for the internal standard 390 are described in U.S. Patent Application, titled "RESOLUTION CONTROL IN X-RAY FLUORESCENCE SPECTROSCOPY SYSTEMS," filed concurrently herewith, which is hereby incorporated by reference herein in its entirety for all purposes. However, where anything in the incorporated reference contradicts anything stated in the present application, the present application prevails.

In some embodiments, the internal standard measurement position shown in FIGS. 2B and 2D is a fail-safe position, that is, a position in which, in the event of a power or air pressure failure, the immersion probe analyzer 110 will raise the carriage assembly 280 with the aid of stored pneumatic air in a receiver tank (not shown). Minimal radiation is emitted from probe head 120 in this position, because the X-ray sources 160 are covered behind shield 285.

Figure 4:
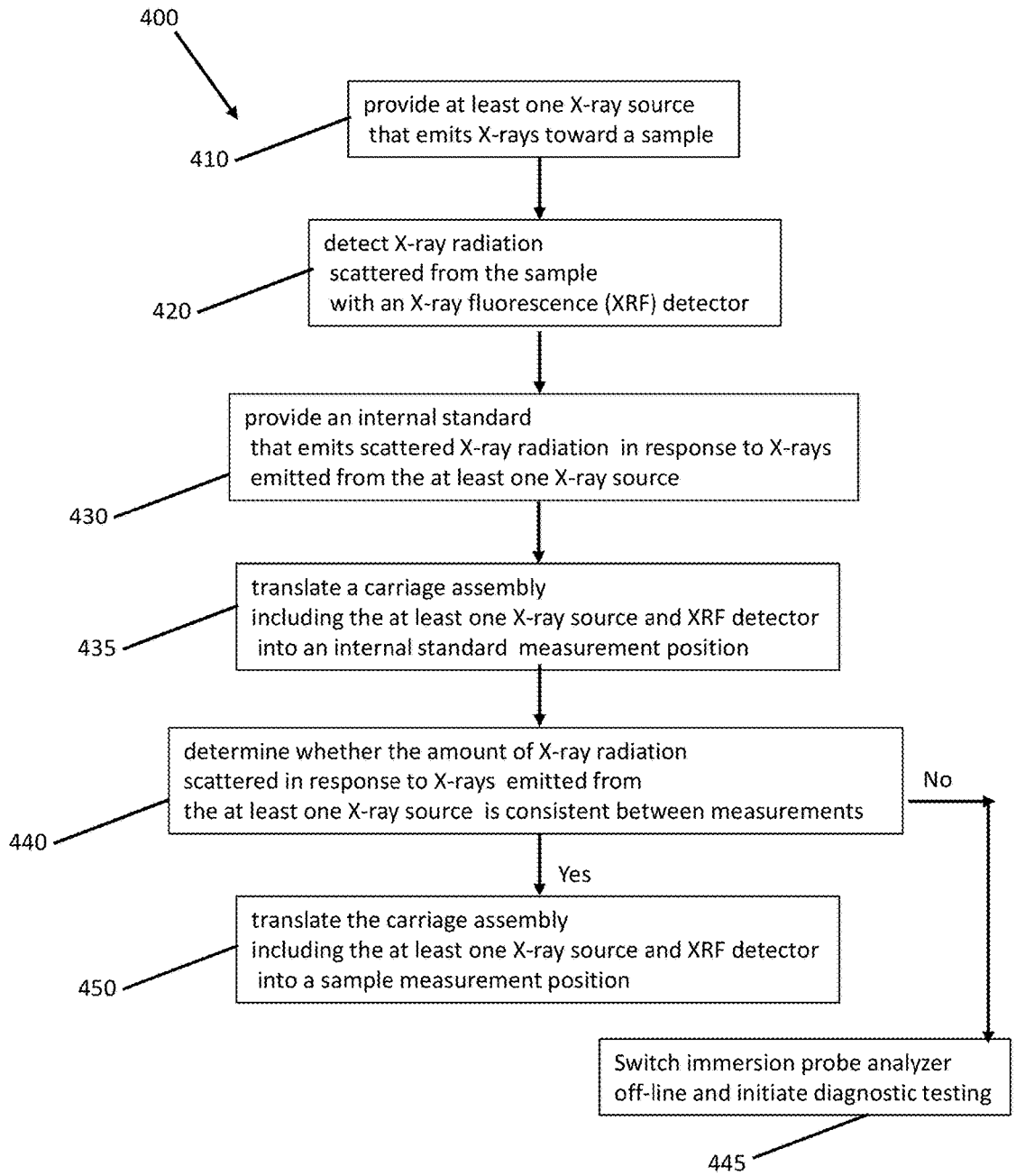
FIG. 4 is a flow chart of an exemplary embodiment of a method of monitoring an XRF detector response to an X-ray source according to the invention.

In another embodiment shown in FIG. 4, a method 400 of monitoring an XRF detector response to an X-ray source in an immersion probe analyzer includes providing at least one X-ray source that emits X-rays toward a sample at step 410, detecting X-ray radiation scattered from the sample with an X-ray fluorescence (XRF) detector at step 420, providing an internal standard that emits scattered X-ray radiation in response to X-rays emitted from the at least one X-ray source at step 430, translating a carriage assembly including the at least one X-ray source and XRF detector into an internal standard measurement position at step 435, and determining whether the amount of X-ray radiation scattered in response to X-rays emitted from the at least one X-ray source is consistent between measurements at step 440. The method includes translating the carriage assembly including the at least one X-ray source and XRF detector into a sample measurement position at step 450 if the stability criterion described above is met. The immersion probe analyzer, at least one X-ray source, internal standard measurement position, internal standard, stability criteria for the internal standard, and XRF detector are as described above.

The method further includes switching the immersion probe analyzer off-line and initiating diagnostic testing at step 445 if the stability criterion is not met, that is, if the amount of scattered X-ray radiation emitted by the internal standard in response to X-rays emitted from the at least one X-ray source is inconsistent between measurements. Diagnostic testing includes checking the air pressure to determine whether the carriage assembly is returning to the same internal standard measurement position after movement between the sample and internal standard measurement positions. Additional or alternative diagnostic testing includes using the external standard to determine whether the amount of X-ray radiation scattered in response to X-rays emitted from the at least one X-ray source is consistent between measurements. If the stability criterion described above is not met with a clean external standard applied with the same tension as for previous measurements to a clean probe window, then the probe is disassembled and the mechanical stability of the X-ray source(s) is checked and/or the XRF detector is replaced.

Other Embodiments

A number of embodiments have been described. Nevertheless, it will be understood that various modifications may be made without departing from the spirit and scope of the disclosure. Accordingly, other embodiments are within the scope of the following claims.

What is claimed is:
1. An apparatus comprising:
   a. at least one X-ray source that emits X-rays toward a sample;
   b. an X-ray fluorescence (XRF) detector that detects X-ray radiation scattered from the sample;
   c. an internal standard that emits scattered X-ray radiation in response to X-rays emitted from the at least one X-ray source; and
   d. a carriage assembly that translates the at least one X-ray source and XRF detector between a sample measurement position and an internal standard measurement position.

2. The apparatus of claim 1, wherein the at least one X-ray source is one or more of a Curium-244 (Cm-244) source, a Plutonium-238 (Pu-238) source, an Americium-241 (Am-241) source, a Cadmium (Cd-109) source, an Iron-55 (Fe-55) source, or any combination thereof.

3. The apparatus of claim 1, wherein the internal standard measurement position is a fail-safe position.

4. The apparatus of claim 1, wherein the internal standard is comprised of a mineral sample powder.

5. The apparatus of claim 4, wherein the mineral sample powder is one of silica, haematite, chalcocite, or any combination thereof.

6. The apparatus of claim 1, wherein the amount of scattered X-ray radiation emitted by the internal standard in response to X-rays emitted from the at least one X-ray source is consistent to less than or equal to 3 parts in a thousand between measurements.

7. The apparatus of claim 1, wherein the XRF detector is one of a silicon drift detector or a PIN diode detector.

8. A method of monitoring an XRF detector response to an X-ray source in an immersion probe analyzer, the method comprising:
   a. providing at least one X-ray source that emits X-rays toward a sample;
   b. detecting X-ray radiation scattered from the sample with an X-ray fluorescence (XRF) detector;
   c. providing an internal standard that emits scattered X-ray radiation in response to X-rays emitted from the at least one X-ray source;
   d. translating a carriage assembly including the at least one X-ray source and XRF detector into an internal standard measurement position;
   e. determining whether the amount of X-ray radiation scattered in response to X-rays emitted from the at least one X-ray source is consistent between measurements; and
   f. translating the carriage assembly including the at least one X-ray source and XRF detector into a sample measurement position.

9. The method of claim 8, wherein the at least one X-ray source is one or more of a Curium-244 (Cm-244) source, a Plutonium-238 (Pu-238) source, an Americium-241 (Am-241) source, a Cadmium (Cd-109) source, an Iron-55 (Fe-55) source, or any combination thereof.

10. The method of claim 8, wherein the internal standard measurement position is a fail-safe position.

11. The method of claim 8, wherein the internal standard is comprised of a mineral sample powder.

12. The method of claim 11, wherein the mineral sample powder is one of silica, haematite, chalcocite, or any combination thereof.

13. The method of claim 8, wherein the amount of scattered X-ray radiation emitted by the internal standard in response to X-rays emitted from the at least one X-ray source is consistent to less than or equal to 3 parts in a thousand between measurements.

14. The method of claim 8, further including initiating diagnostic testing of the immersion probe analyzer if the amount of scattered X-ray radiation emitted by the internal standard in response to X-rays emitted from the at least one X-ray source is inconsistent between measurements.

15. The method of claim 8, wherein the XRF detector is one of a silicon drift detector or a PIN diode detector.

16. An XRF immersion probe analyzer comprising:
   a. a probe head immersible into and resistant to an ore slurry, the probe head including an X-ray transparent window;
   b. a probe including:
     i. at least one X-ray source that emits X-rays toward a sample through the window;
     ii. an X-ray fluorescence (XRF) detector that detects X-ray radiation scattered from the sample through the window;
   c. an internal standard that emits scattered X-ray radiation in response to X-rays emitted from the at least one X-ray source; and
   d. a carriage assembly that translates the at least one X-ray source and XRF detector between a sample measurement position in the probe head and an internal standard measurement position.

17. The XRF immersion probe analyzer of claim 16, wherein the at least one X-ray source is one or more of a Curium-244 (Cm-244) source, a Plutonium-238 (Pu-238) source, an Americium-241 (Am-241) source, a Cadmium (Cd-109) source, an Iron-55 (Fe-55) source, or any combination thereof.

18. The XRF immersion probe analyzer of claim 16, wherein the probe is a multi-element probe.

19. The XRF immersion probe analyzer of claim 16, wherein the internal standard measurement position is a fail-safe position.

20. The XRF immersion probe analyzer of claim 16, wherein the internal standard is comprised of a mineral sample powder.

21. The XRF immersion probe analyzer of claim 20, wherein the mineral sample powder is one of silica, haematite, chalcocite, or any combination thereof.

22. The XRF immersion probe analyzer of claim 16, wherein the amount of scattered X-ray radiation emitted by the internal standard in response to X-rays emitted from the at least one X-ray source is consistent to less than or equal to 3 parts in a thousand between measurements.

23. The XRF immersion probe analyzer of claim 16, wherein the XRF detector is one of a silicon drift detector or a PIN diode detector.

* * * * *